(12) United States Patent
Inoue et al.

(10) Patent No.: US 7,304,730 B2
(45) Date of Patent: Dec. 4, 2007

(54) INSPECTION APPARATUS HAVING TWO SENSORS, METHOD FOR INSPECTING AN OBJECT, AND A METHOD FOR MANUFACTURING A PHOTOLITHOGRAPHY MASK

(75) Inventors: Hiromu Inoue, Kanagawa-ken (JP); Toru Tojo, Kanagawa-ken (JP); Takehiko Nomura, Kanagawa-ken (JP); Shinichi Imai, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 311 days.

(21) Appl. No.: 10/852,434

(22) Filed: May 25, 2004

(65) Prior Publication Data

US 2005/0002020 A1 Jan. 6, 2005

(30) Foreign Application Priority Data

May 27, 2003 (JP) .............................. 2003-149336

(51) Int. Cl.
*G01N 21/00* (2006.01)
(52) U.S. Cl. ............................... 356/237.1; 356/237.4; 356/237.5
(58) Field of Classification Search .. 356/237.1–237.6, 356/445, 600
See application file for complete search history.

(56) References Cited

U.S. PATENT DOCUMENTS

| | | | |
|---|---|---|---|
| 5,017,798 A * | 5/1991 | Murakami et al. ..... | 250/559.06 |
| 5,892,579 A * | 4/1999 | Elyasaf et al. ........... | 356/239.8 |
| 6,175,645 B1 * | 1/2001 | Elyasaf et al. .............. | 382/147 |
| 6,597,001 B1 * | 7/2003 | Yamashita et al. ....... | 250/491.1 |
| 6,727,987 B2 * | 4/2004 | Yonezawa ................ | 356/237.2 |
| 6,879,390 B1 * | 4/2005 | Kvamme et al. ........ | 356/237.2 |
| 2003/0063274 A1 * | 4/2003 | Tsai et al. ................ | 356/237.5 |
| 2004/0027563 A1 * | 2/2004 | Elyasaf et al. ........... | 356/237.1 |

FOREIGN PATENT DOCUMENTS

| | | |
|---|---|---|
| JP | 06-294750 | 10/1994 |
| JP | 07-190945 | 7/1995 |
| JP | 10-123059 | 5/1998 |
| JP | 10-178300 | 6/1998 |
| JP | 2002-501194 | 1/2002 |

\* cited by examiner

Primary Examiner—Gregory J. Toatley, Jr.
Assistant Examiner—Tri Ton
(74) Attorney, Agent, or Firm—Finnegan, Henderson, Farabow, Garrett & Dunner, L.L.P.

(57) ABSTRACT

A photolithography mask inspection apparatus has at least two sensors. One sensor is configured to sense light transmitted through an object to be inspected, and the other sensor senses light reflected off the object. A first optical system is arranged to expose a first portion of the object with a first light beam, and a second optical system is arranged to expose a second portion of the object, spaced form the first portion, with a second light beam. A third optical system focuses the transmitted light on to the first sensor, as well as the reflected light on to the second sensor. A defect detecting circuit is also provided to detect a defect of the object, based upon image data associated with the reflected and transmitted light.

8 Claims, 13 Drawing Sheets

FIG. 13 PRIOR ART

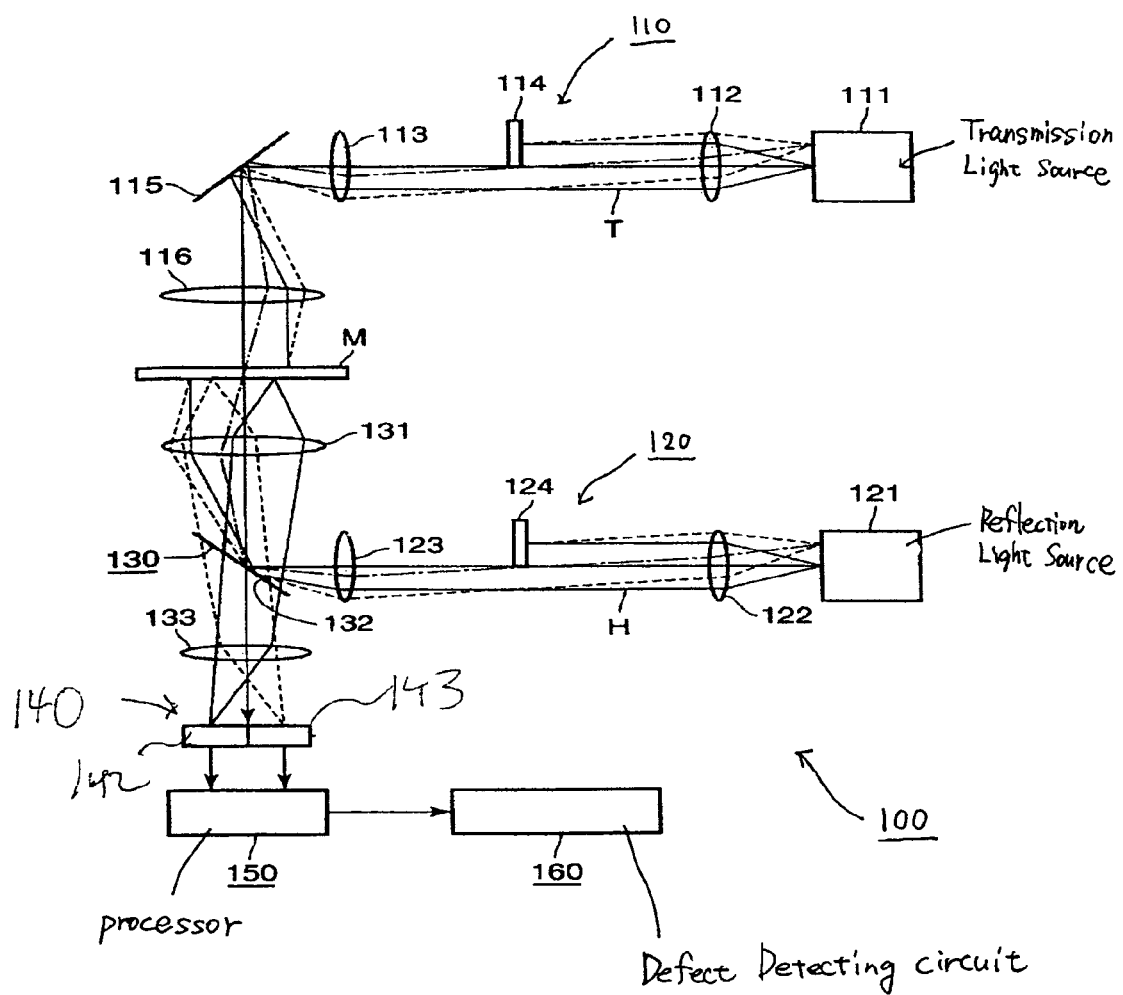

INSPECTION APPARATUS HAVING TWO SENSORS, METHOD FOR INSPECTING AN OBJECT, AND A METHOD FOR MANUFACTURING A PHOTOLITHOGRAPHY MASK

CROSS REFERENCE TO RELATED APPLICATION

This application is based upon and claims the benefit of priority from prior Japanese Patent Application No. 2003-149336 filed on May 27, 2003, the entire contents of which are incorporated herein by reference.

1. Field of the Invention

The present invention relates to an inspection apparatus having a first sensor to sense a transmitted image of an object to be inspected and a second sensor to sense a reflected image of the object. The present invention is also directed toward a method for inspecting an object, and a method for manufacturing a mask.

2. Description of the Related Art

Conventional inspection systems detect defects in an object, such as a semiconductor device or photo-mask (e.g., a photolithography mask) by comparing an image of the object corresponding to light transmitted through the transmitted image of the object with a reference pattern. However, certain defects, such as thin film on a residue on a half-tone film or a minimum pin hole defect, are difficult to detect with such systems. Accordingly, alternative inspection systems having improved performance have been developed which compare a transmitted image of the object with an image of the object corresponding to light reflected off the object. FIG. 10 is a schematic diagram of an optical system including inspection apparatus 10 having a first sensor that senses a light transmitted through the object and a second sensor that detects light reflected from the object. Apparatus 10 includes an optical source 11, which outputs light that passes through collector lens 12, half mirror 13 and condenser/objective lens 14 to mask M. Some of the light impinging on mask M is transmitted through the mask, and some is reflected. The transmitted light constitutes an image of mask M that passes through an additional objective lens 15, which focuses the light onto sensor 16. In addition, light reflected off mask M (the reflected image) passes back through lens 14, and is further reflected off mirror 13 to second sensor 17. Lens 14 is configured to focus the reflected light onto sensor 17. Defects are then detected based on the outputs of sensors 16 and 17 in accordance with the transmitted and reflected images, respectively. As further shown in FIG. 10, mask M is positioned between lenses 14 and 15.

FIG. 11 illustrates a schematic diagram of an alternative conventional mask inspection apparatus 20 having a transmission light source 21 and a reflection light source 29. Light emitted from source 21 passes through lens 22 and is reflected off mirror 23, which directs the light to mask M through condenser lens 24. Light passing through mask M also passes through objective lens 25 and half mirror 26, and is focused by image-forming lens 27 onto sensor 28.

Light emitted by reflection source 29 passes through lens 30, and is reflected off mirror 26 to mask M through objective lens 25. Light reflected off mask M passes back through lens 25, and is transmitted through half mirror 26, and then focused onto sensor 28 with image-forming lens 27. As further shown in FIG. 11, mask M, under inspection, is arranged between condenser lens 24 and objective lens 25.

In addition, both the transmitted image and the reflected image of mask M are sensed by single sensor 28. Defects are detected based on an output of sensor 28. FIG. 12 illustrates a schematic diagram of another conventional optical system including a mask inspection apparatus 40, which exposes the mask to laser light having a relatively short wavelength, and identifies defects based on sensing both reflected and transmitted images of an object. Apparatus 40 includes a laser light source 41, beam expander 42, a conventional speckles reduction system 43, a collector lens 44, and a half mirror 45. Speckles reduction system 43 minimizes speckles, as described in which is disclosed in Japanese Patent Disclosure (kokai) No. 10-178300. Half mirror 45 separates laser light output from source 41 into a first laser beam which propagates along an optical path R, and a second laser beam which propagates along an optical path Q. The first laser beam travels along an optical path R including collector lens 46, mirror 47, condenser 48, objective lens 49 and a half mirror 50, and the second laser beam is reflected by mirror 51 to condenser lens 52 provided along optical path Q. The second laser beam is then reflected by mirror 50 toward mask M through lens 49.

In operation, the transmitted image of mask M, corresponding to a portion of the first laser beam transmitted through mask M, passes through lens 9 and half mirror 50. The transmitted image is next focused by lens 53 onto sensor 54, which are provided on a transmission surface side of half mirror 50. In addition, the second beam is reflected off mask M back through lens 49, half mirror 50 and lens 53. The reflected second beam off mask M constitutes a reflected image of the mask, which is focused by lens 53 onto sensor 54. Defects are then located based on the sensed transmitted and reflected images.

FIG. 13 illustrates an additional conventional optical system including inspecting apparatus 60 having a laser light source 61. Apparatus 60 can also sense both reflected and transmitted images of an object. In apparatus 60, however, a polarization plane of a light beam transmitted through the mask is rotated by 90 degrees relative to light beam reflected by the mask.

As further shown in FIG. 13, mask inspecting apparatus 60 is provided with a laser light source 61, a beam expander 62, a speckles reducing system 63, a collector lens 64, and a half mirror 65. Speckles, which are caused by optical interference in the S-polarized laser beam are reduced by speckles reducing system 63 after being expanded in diameter by beam expander 62. Half mirror 65 separates a laser beam from laser light source 61 into a first S-polarized laser beam propagating along an optical path R, and a second P-polarized laser beam traveling along an optical path Q. Optical path R includes λ/4 wavelength plate 66, collector lens 67, mirror 68, condenser lens 69, objective lens 70, an additional λ/4 wavelength plate 71 and half mirror 72, and optical path Q includes λ/2 wavelength plate 73, mirror 74, condenser lens 75. A laser beam propagating along optical path Q enters a reflection surface of half mirror 72 and is reflected to mask M through λ/4 plate 71 through lens 70. The first laser beam, after passing through mask M along path R, constitutes a transmitted image of the mask, which is focused onto mirror 72 via λ/4 plate 71. Moreover, the second beam forms a reflected image of mask M after reflection off mask M. The reflected image is also focused onto mirror 72 through λ/4 plate 71 by lens 70.

Both the reflected and transmitted images pass through half-mirror 72, and then to polarization beam splitter (PBS) 76, which separates and reflects the P-polarized second beam to sensor 80 through image-forming lens 79. In addition, PBS 76 directs the S-polarized first laser beam to sensor 78 via lens 77.

Accordingly, sensor 78 senses the transmitted image, and sensor 80 receives the reflected image of mask M, which is provided between condenser lens 69 and objective lens 70. Defects are then determined based on the sensed transmitted and reflected images of mask M.

A further inspecting system is disclosed in Japanese Patent Disclosure (kokai) No. 6-294750, which also simultaneously generates transmitted and reflected images, but uses a beam scanning method. Japanese Patent Disclosure (kokai) No. 10-123059, obtains a reflected and transmitted images of an object by switching at a high speed between two light sources, one being a transmission light source, and the other a reflection light source.

The mask inspection systems described above, however, suffer from various shortcomings, as discussed below. Inspection systems 20 and 40 (FIGS. 11 and 12) have a single sensor, which detects both transmitted and reflected images. These systems can be configured to alternately sense the transmitted and reflected images with sensor 28 (FIG. 11) or sensor 54 (FIG. 12), but typically require twice as much time to detect defects in mask M than the system shown in FIG. 10 having only one sensor.

Inspection systems 20 and 40 can be configured to sense both the reflected and transmitted images simultaneously. In which case, defects can be detected in substantially the same amount of time as systems that sense only a transmitted image or reflected image of the object (see for example, FIG. 10 illustrating an inspection system that only senses the transmitted image). However, simultaneous detection of the reflected and transmitted images requires that the two images be combined or added to one another to form a composite image. When combined, the transmitted and reflected images can interfere and cancel the defect signal with one another, thereby creating so-called "dead zones" in the composite image where defects many not be detected.

The mask inspecting systems shown in FIGS. 10 and 13 overcome the above-described drawbacks of single sensor-based detection. These systems, however, require complex optics for focusing the transmitted and reflected image optics on to corresponding sensors. In addition, simultaneous sensing of reflected and transmitted images is further complicated by different optical systems i.e., the transmitted and reflected optics include different components, which create different distortions in the sensed transmitted and reflected images. In addition, these differences may cause the reflected and transmitted images to be magnified differently.

Beam scanning inspection techniques have also been developed whereby a laser beam is scanned across a photolithography mask, and light reflected from exposed portions of the mask is detected. In order to finely resolve narrow mask patterns, however, relatively short wavelengths of laser light are required. Such light, however, is more energetic than lower wavelength light, and can damage the photolithography mask, especially if the laser light wavelength is less 250 nm.

In addition, in the system shown in FIG. 11, transmission and reflection light sources 21 and 29 may be switched on an off to alternately supply light to mask M. Such switching between sources 21 and 29, however, may result in an excessive amount of time to complete mask inspection.

SUMMARY OF THE INVENTION

One aspect of the present invention is an apparatus. The apparatus has a first optical system configured to expose a first portion of the object with a first light beam, and a second optical system configured to expose a second portion of the object with a second light beam. The second portion of the object being substantially spaced from the first portion. The apparatus comprises a first sensor configured to sense a transmitted image of the first portion of the object. The transmitted image corresponds to a portion of the first light beam passing through the first portion of the object, and the first sensor generates first image data in response to the transmitted image. The apparatus also comprises a second sensor configured to sense a reflected image of the second portion of the object, the reflected image corresponding to a portion of the second light beam reflected off the second portion of the object. The second sensor generates second image data in response to the reflected image. A third optical system is provided which is configured to focus the transmitted image on to the first sensor, and focus the reflected image on to the second sensor. In addition a defect detecting circuit is provided which is configured to detect a defect of the object based upon the first and second image data.

Another aspect of the present invention is a method for inspecting an object. The method includes steps of exposing a first portion of the object with a first light beam, and exposing a second portion of the object with a second light beam the second portion being spaced from the first portion. In a further step, the transmitted image of the mask is sensed with a first sensor, the transmitted image corresponding to a portion of the first light beam passing through the object. The method also includes a step sensing a reflected image of the mask with a second sensor, the reflected image corresponding to a portion of the second light beam reflected off the object, and a step of identifying defects associated with the object based upon the transmitted and reflected images.

In accordance with a further aspect of the present invention, a method of manufacturing a mask is provided Comprising steps of fabricating a mask by forming a pattern on a substrate, and inspecting the mask. The inspection step comprises the object inspection steps described above.

BRIEF DESCRIPTION OF THE DRAWING

FIG. 1 is a schematic diagram of a mask inspection apparatus 100 consistent with an aspect of the present invention;

DETAILED DESCRIPTION OF THE INVENTION

Figure 2A:
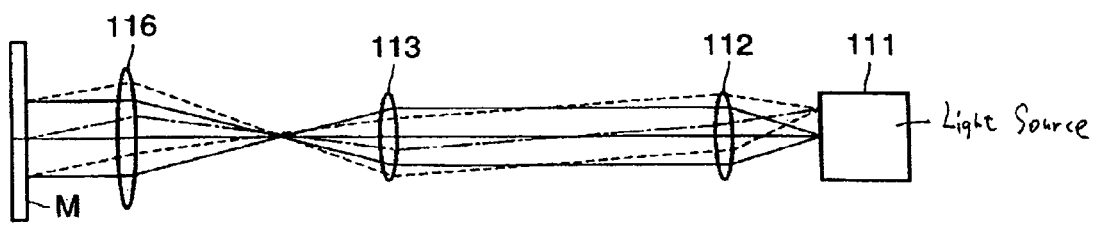
FIG. 2A shows an optical path of a light beam emitted from a light source 111 when a first aperture 114 is removed from first optical system 110 consistent with a further aspect of the present invention.

Reference will now be made in detail to exemplary embodiments of the invention, examples of which are illustrated in the accompanying drawings. Wherever possible, the same reference numbers will be used throughout the drawings to refer to the same or like parts.

FIG. 1 shows a schematic diagram of a mask inspection apparatus 100 for inspecting a mask M. Mask inspection apparatus 100 includes a first and second optical systems 110 and 120. Optical system 120 includes imaging optics 130, a sensor device 140 for sensing both transmitted and a reflected images, a processor 150 for processing image data output from sensor device 140, and defect detecting circuit 160 for detecting a defect in mask M.

Optical system 110 includes a transmission light source (first light source) 111, which emits a light beam T. A pair of collector lenses 112 and 113 are spaced from one another with a first aperture 114 provided there between. Light beam T first passes through collector lens 112 and a portion of the beam (typically about half) is blocked. A remaining portion of light beam T next passes through collector lens 113. System 110 also includes a mirror 115 for directing light beam T toward mask M, and a condenser lens 116 for projecting light beam T onto a portion of mask M. Since half of beam T is blocked by aperture 114, approximately half of the area which would have been exposed by beam T without aperture 114, is exposed by the remaining portion of beam T. A portion of beam T passing through mask M constitutes a partial transmitted image of the mask.

Second optical system 120 includes a reflection light source (second light source) 121 that outputs light beam H. A pair of collector lenses 122 and 123 are spaced from one another with a second aperture 124 provided there between. After passing through collector lens 122, a portion, typically about half, of beam H is blocked by a second aperture 124. Accordingly, as discussed below, about half of the area which would have been exposed by light T without aperture 124, is exposed by beam H on a side of mask M opposite the side exposed by beam T.

Imaging optics (third optical system) 130 is provided with an objective lens 131, a half mirror 132 and an image-forming lens 133. Objective lens 131, functioning as a condenser lens, projects the unblocked portion of beam H onto mask M. Objective lens 131 also enlarges an optical image of mask M by refracting a portion of light beam H reflected off mask M, and a portion of light beam T which passes through mask M.

Half mirror 132 directs the remaining portion of light beam H toward mask M, where a further portion of the beam is reflected off mask M. Light reflected off mask M constitutes a partial reflected image of the mask corresponding to a reflected partial image of the mask.

Next, objective lens 131 enlarges the partial reflected and transmitted images of mask M by refracting both portions of light beam H reflected off mask M and light beam T which passes through mask M, and the partial reflected and transmitted images next pass through half mirror 132, and the partial reflected and transmitted images of mask M are focused onto sensor device 140, including first and second sensors 142 and 143, respectively, by image-forming lens 133.

Figure 6A:
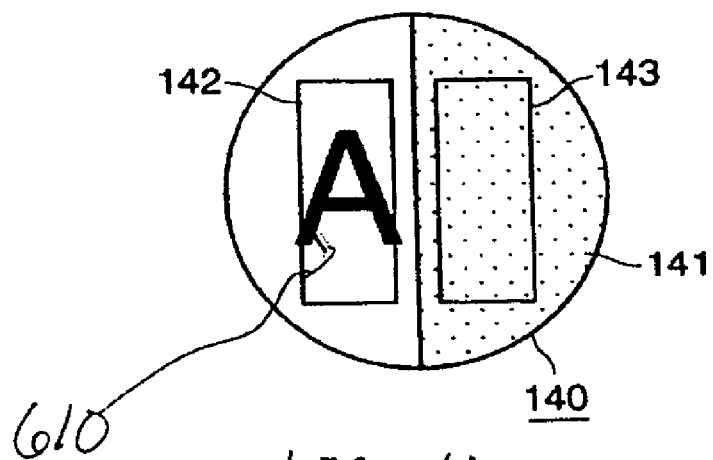
FIGS. 6A and 6B shows a pattern "A" of mask M, which is sensed by both the first and second sensors 142 and 143, in accordance with an additional aspect of the present invention.
Figure 6B:
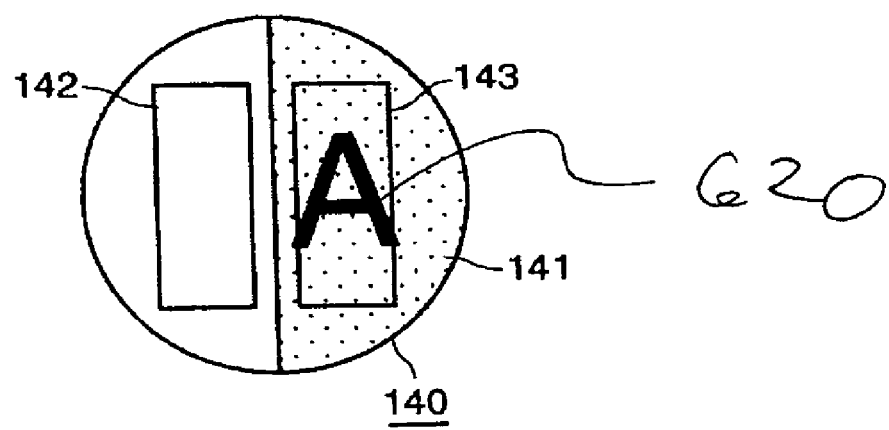

As shown in FIGS. 6A and 6B, sensor device 140 includes base 141, and first sensor 142 secured to base 141 for sensing the transmitted partial image corresponding to a portion of light beam T. A second sensor 143 is also secured to base 141 for sensing the partial reflected image corresponding to a portion of light beam H. The sensors typically include conventional time delay integration (TDI) sensors, but other known sensors can be used, such as area or line-sensors(e.g., an one-dimensional sensor), can be used as well instead of the TDI sensor.

First and second sensors 142 and 143 are typically arranged in parallel. The two sensors are positioned relatively close or adjacent to one another and the distance between them is preferably minimal. Sensor device 140 can be assembled by manufacturing sensors 142 and 143 separately, followed by mechanical positioning and mounting of each sensor onto base 141. Optionally, one sensor may be provided onto base 141, and the second sensor may be positioned onto base 141 at a location relative to the first sensor. Alternatively, the two sensors may be integrally manufactured adjacent one another on the same wafer, integrally cut by a dicing cutter, and mounted on base 141.

Figure 7:
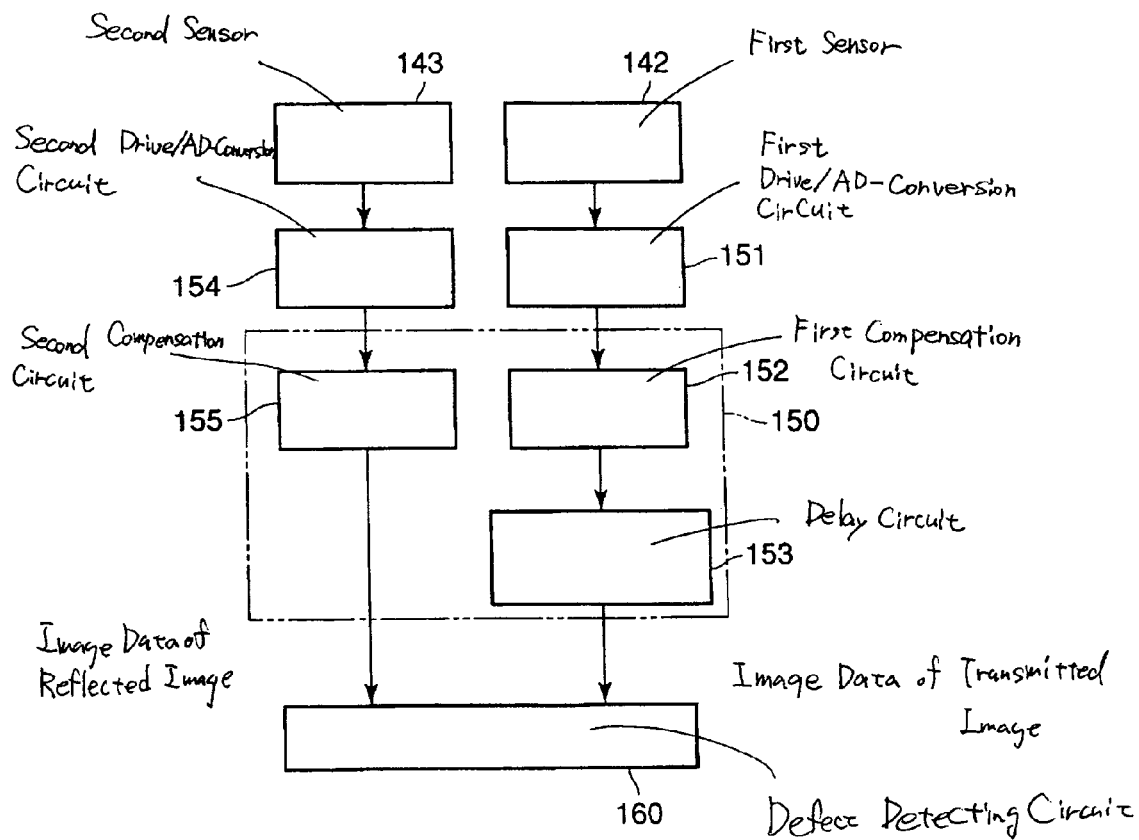
FIG. 7 shows a schematic view of an exemplary processor 150 and a defect detecting circuit 160 in connection with the apparatus shown in FIG. 1.

FIG. 7 illustrates processor circuit 150 in greater detail. Processor 150 is electrically connected to both a first drive/AD-conversion circuit 151 and a second drive/AD-conversion circuit 154. First circuit 151 drives first sensor 142, and converts an analog image signal from sensor 142 into digital image data. Second circuit 154 drives second sensor 143, and converts an analog image signal from sensor 143 into digital image data.

Processor 150 includes a first compensation circuit 152, a second compensation circuit 155 and a delay circuit 153. First compensation circuit 152 compensates output characteristics of image data from circuit 151 by adjusting gain, offset and other suitable parameters associated with the output of first drive/AD conversion circuit 151. In addition, second compensation circuit 155 compensates output characteristics of image data from circuit 154 by adjusting gain, offset and other suitable parameters associated with the output of second drive/AD conversion circuit 154. Delay circuit 153 delays image data obtained by sensor 142 so as to output the image data at substantially the same time as with image data obtained by second sensor 143.

The operation of mask inspection apparatus 100 will next be explained.

First, mask M to be inspected is set in a predetermined position. Transmission and reflection light sources 111 and 121 next output light beams T and H, first and second light beams, respectively.

In the example above, about half of light beam T is blocked by aperture 114, resulting in about half of the area which would have been exposed in the absence of aperture 114, being exposed. Such partial exposure will next be described in greater detail with reference to FIGS. 2A and 2B.

Figure 2B:
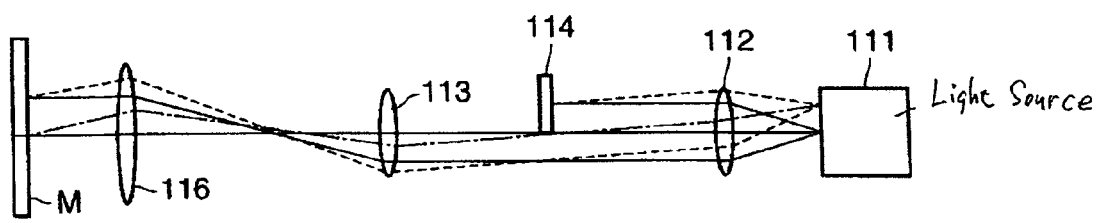
FIG. 2B shows an optical path of a light beam emitted from a light source 111 when a first aperture 114 is arranged along the optical path, in accordance with an aspect of the present invention.

FIG. 2A shows an optical path of a light beam emitted from light source 111 without aperture 114, whereby mask M is exposed through Koehler illumination. FIG. 2B shows an optical path of a light beam emitted from light source 111 in which aperture 114 is provided between lenses 112 and 113, as in FIG. 1.

As further seen in FIG. 2A, light source 111 emits a light beam, which is focused with collector lenses 112 and 113, and projected onto mask M by condenser lens 116. Light source 111 can be considered as a collection of individual point source emitters, each of which outputting a corresponding light beam. Light beams emitted from each emission point of one single light source expose the same area on mask M under Koehler illumination. Therefore, it is possible to reduce an exposed area on mask M by arranging an aperture at a conjugated position of the projection plane.

FIG. 2B illustrates emission from light source 111 when first aperture 114 is provided along an optical path between lenses 112 and 113. In the example shown in FIG. 2B, half of the area which would have been exposed under no aperture 114, is exposed by arranging aperture 114 to shield or block half the emitted light at the conjugated position of the projection plane. In a similar fashion, light beam H is blocked by aperture 124 to result in exposure of half of the area which would have been exposed under no aperture 114. The exposed area is opposite the surface exposed by a portion of beam T.

Accordingly, both partial transmitted and reflected images of mask M are enlarged by a single objective lens 131 since the area (first portion) exposed by first optical system 110, is spaced from the area (second portion) exposed by second optical system 120. The partial transmitted image of mask M (propagating along a path represented by a solid line in FIG. 3) is focused onto first sensor 142 by image forming lens 133, which also focuses the partial reflected image (propagating along a path represented by a dashed line in FIG. 3)onto second sensor 143. As further shown in FIG. 3, the partial transmitted and reflected images are spatially close to one another in plane X where lens 131 is located and may overlap.

Figure 4A:
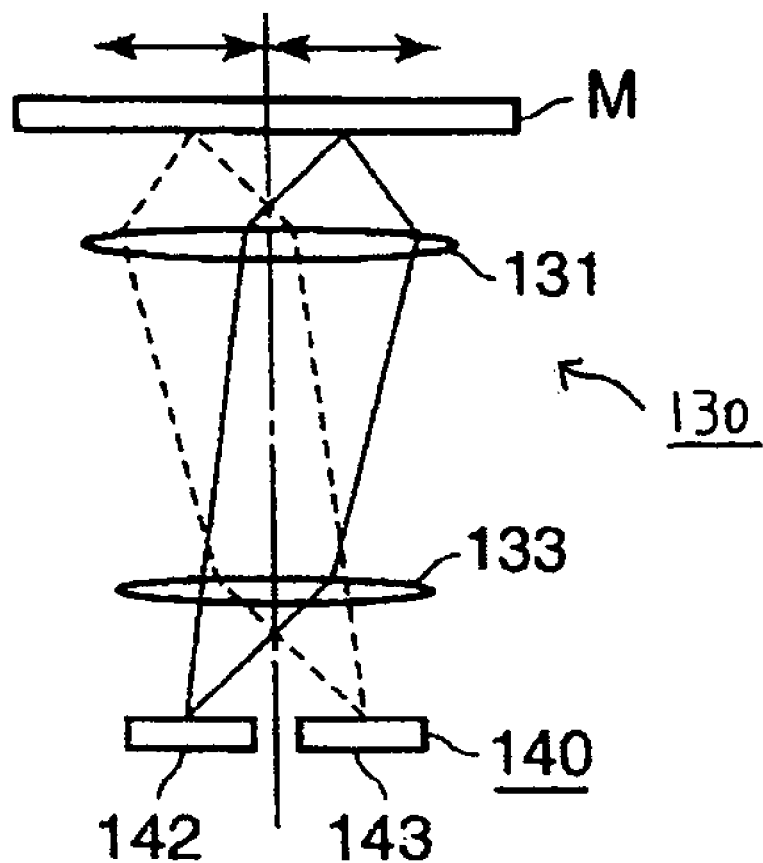
FIG. 4A is a side view showing a mask M, forming optics 130 and a sensor device 140, in accordance with an additional aspect of the present invention.
Figure 4B:
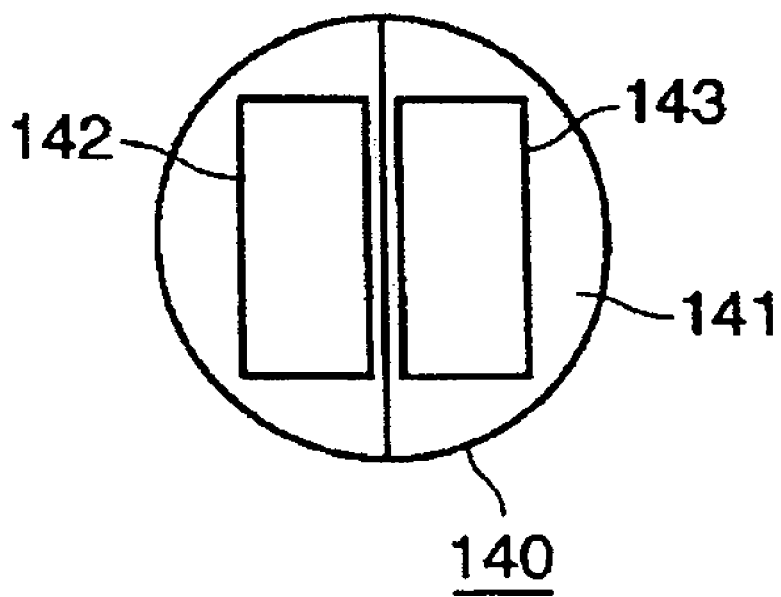
FIG. 4B is a rear view of sensor device 140 consistent with an aspect of the present invention.

FIGS. 4A and 4B show a relationship between locations of sensors 142 and 143, and areas exposed by portions of light beams T and H.

Figure 3:
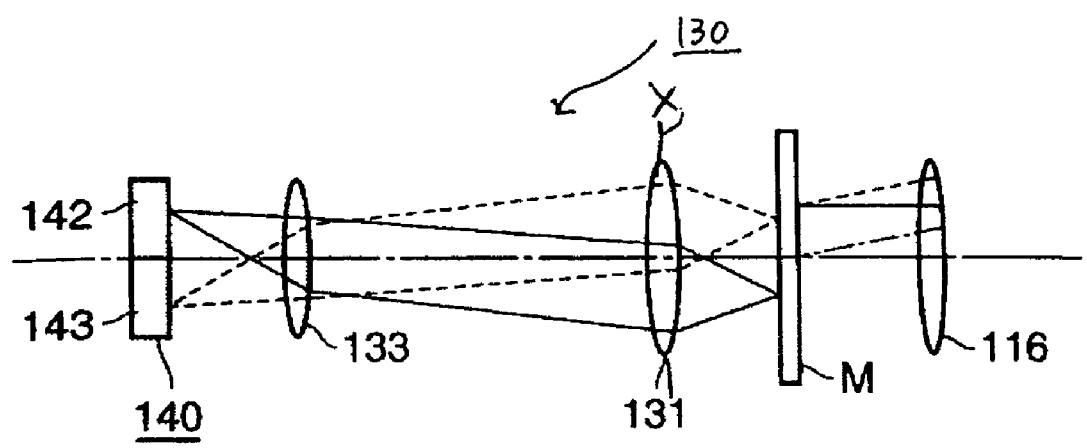
FIG. 3 shows an optical path formed by forming optics 130.

FIG. 4A is a side view showing mask M, forming optics 130 and sensor device 140, rotated counterclockwise from the view shown in figure of FIG. 3 by 90 degrees, and FIG. 4B is a rear view of sensor device 140 from a perspective of sensor 140 receiving portions of beams T and H.

When a right portion of mask M is exposed by light beam T, the partial transmitted image which is enlarged by objective lens 13 is focused on first sensor 142. At the same time, a left portion of mask M exposed by light beam H, is focused on second sensor 143. Each of the exposed areas of mask M is spaced apart from one another by a relatively small amount, or may overlap, and sensors 142 and 143 are arranged close together, as well. Accordingly, imaging optics 130 can focus both images on each of the sensors.

Accordingly, apertures 114 and 124 and the angles associated therewith should be positioned accurately. Sensor device 140 and sensors 142 and 143 should be also precisely positioned.

Figure 5:
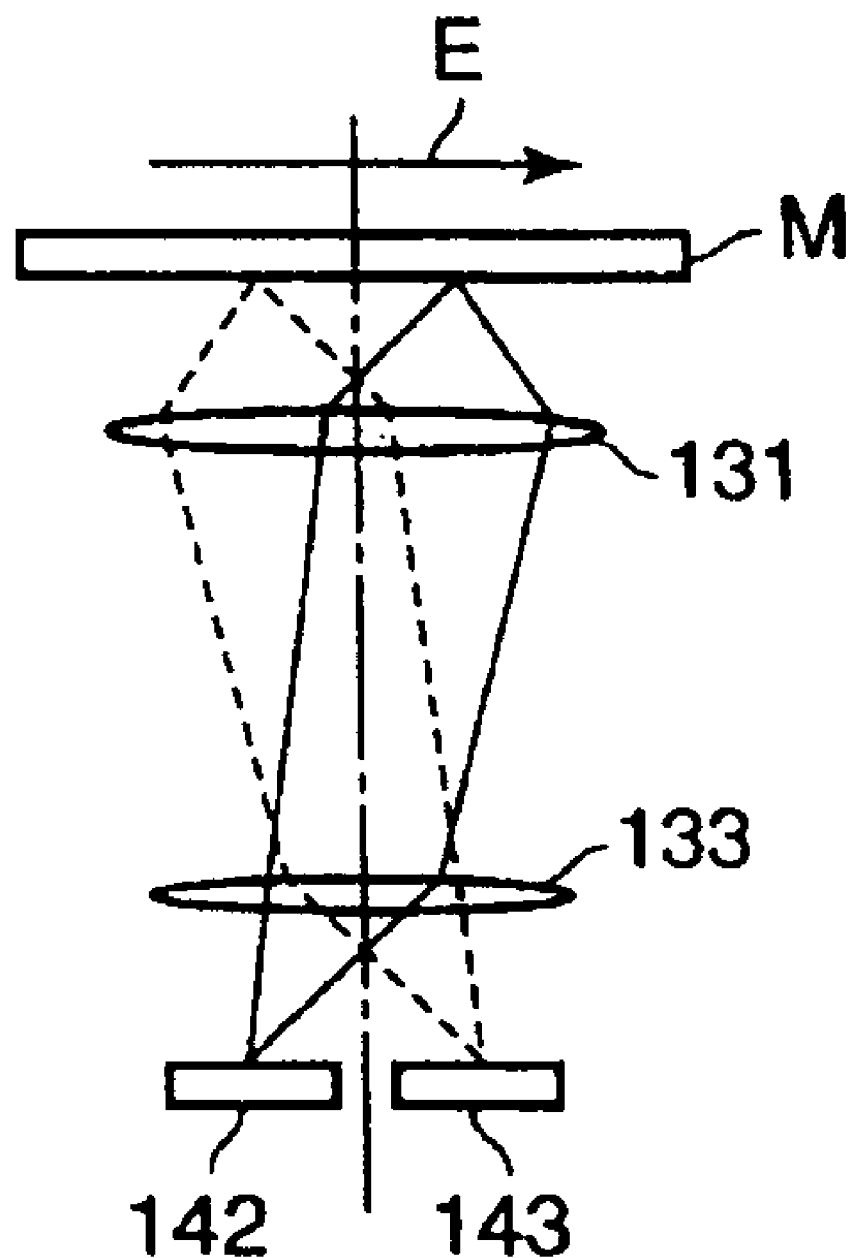
FIG. 5 shows a relationship between a moving direction E of mask M and a first and second sensors 142 and 143 consistent with an aspect of the present invention.

FIG. 5 shows a relationship between a moving direction of mask M, represented by arrow E in FIG. 5, and sensor device 140. First and second sensors 142 and 143 are arranged along direction E. Accordingly, as mask M moves, a transmitted image of a certain portion of mask M is first sensed by first sensor 142, and then a reflected image of the same portion of mask M is sensed by second sensor 143.

For example, as shown in FIG. 6A, a transmitted image 610 of a pattern "A" in mask M is first sensed by first sensor 142 as shown in FIG. 6A. Then, a reflected image 620 of the pattern "A" is sensed by second sensor 143, as shown in FIG. 6B. In a similar fashion, all the patterns contained in mask M are scanned with light beams H and T by moving mask M in horizontal directions.

Returning to FIG. 7, image signals output from first and second sensors 142 and 143, are respectively converted to digital image data by circuits 151 and 154. The output characteristics of the digital image data are compensated by circuit 152 and 155, respectively.

Delay circuit 153 delays an output of image data of a transmitted image to coincide with the image data of a corresponding reflected image. As a result, the delay time depends on the distance between sensors 142 and 143, and the speed of mask M relative to the sensors. Therefore, the image data of the partial transmitted and reflected images are supplied to defect detecting circuit 160 at substantially the same time.

Moreover, since first and second sensors 142 and 143, are arranged in parallel relative to one another, the delay associated with the reflected image data can be readily determined based upon the speed of mask M, the distance between sensors 142 and 143 and the magnification of imaging optics 130.

Figure 8A:
FIG. 8A shows image data output from first sensor 142 consistent with an aspect of the present invention.
Figure 8B:
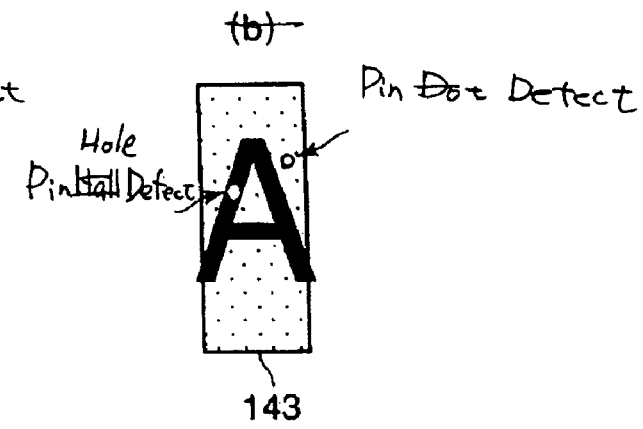
FIG. 8B shows image data output from second sensor 143 consistent with an aspect of the present invention.

FIG. 8A shows image data output from first sensor 142, and FIG. 8B shows an image data output from second sensor 143. Even though both image data correspond to the same mask pattern, the image data is different, because signal intensity is reversed between a transmitted and reflected images.

A transmitted image of a minimum pin hole defect may not have a sufficient signal level or intensity to be detected. However, a reflected image of the minimum pin hole defect has an adequate signal level, and is thus detectable based on the partial reflected image of mask M.

As discussed above, detection based on both transmitted and reflected images is more accurate than detection based on either image alone. In the first embodiment explained above, imaging optics 130 focuses both a partial transmitted image on first sensor 142 and a partial reflected image on second sensor 143. Accordingly, mask M can be inspected based on detection of both reflected and transmitted images at the same time after sensor output delays image data output from first compensation circuit 152 corresponding to sensor 142, for example. In addition, both reflected and transmitted images are subject to the same distortions and defects of common imaging optics 130, thereby minimizing variations between the images that would otherwise occur if the images were sensed by separate optics. In view of the foregoing, defects can be detected and a high quality mask can be manufactured by inspecting the mask with the apparatus 100 following mask fabrication.

Figure 9:
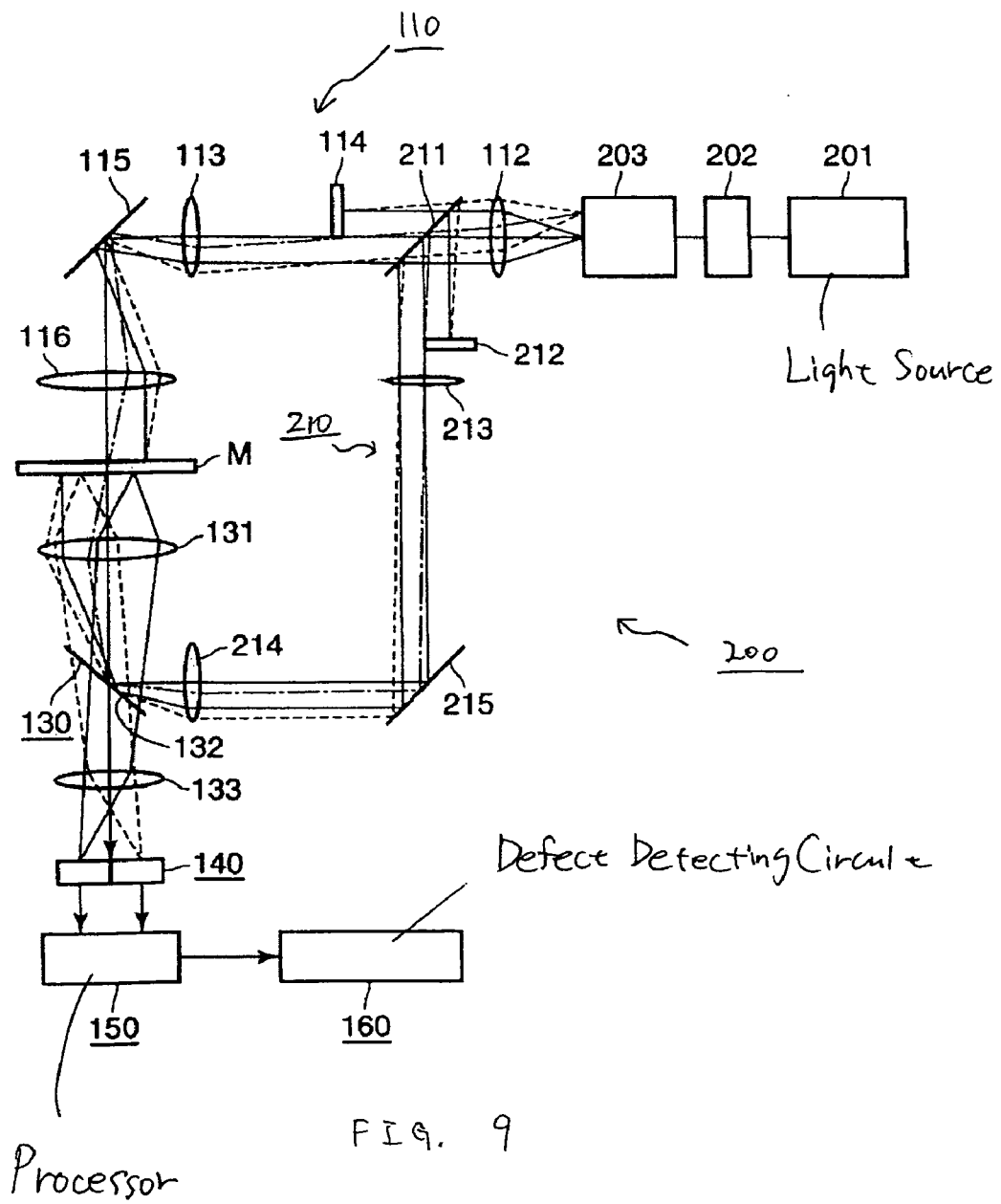
FIG. 9 is a diagram of a mask inspection apparatus 200, consistent with a further aspect of the present invention.
Figure 10:
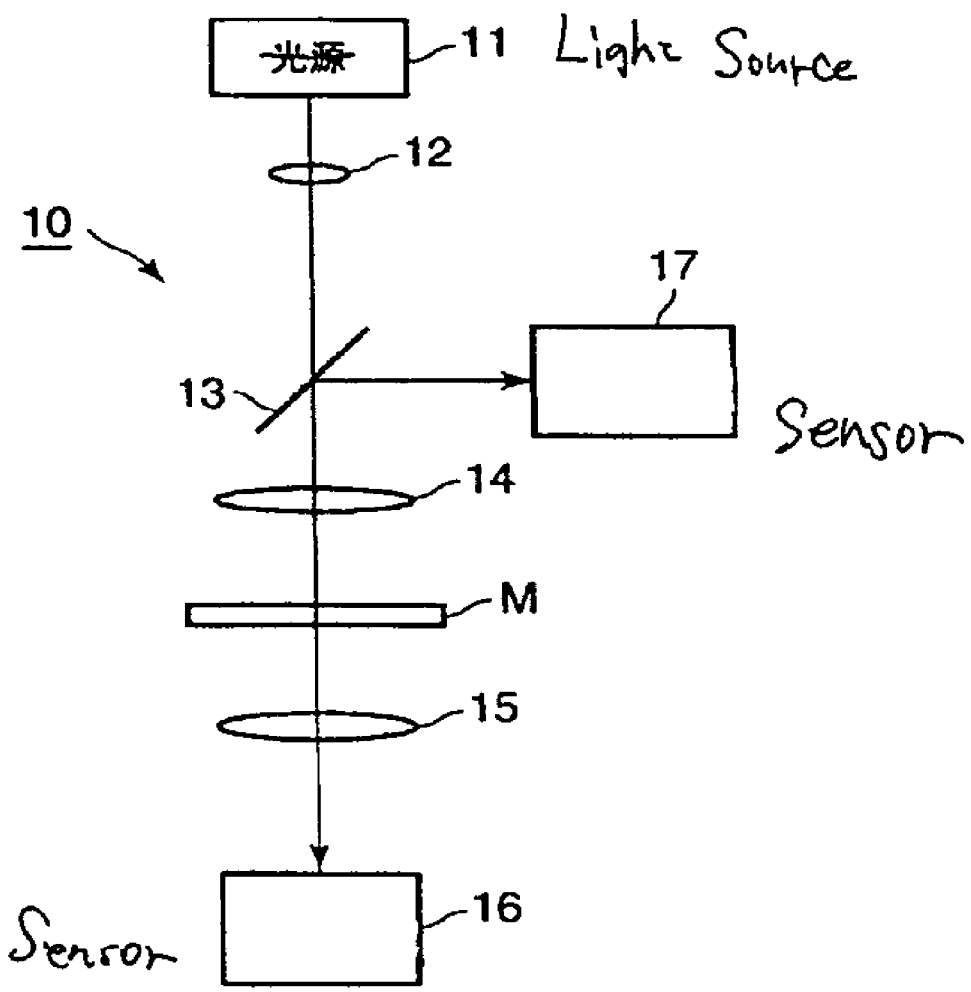
FIG. 10 shows a schematic view of a conventional inspecting apparatus 10 having two sensors.
Figure 11:
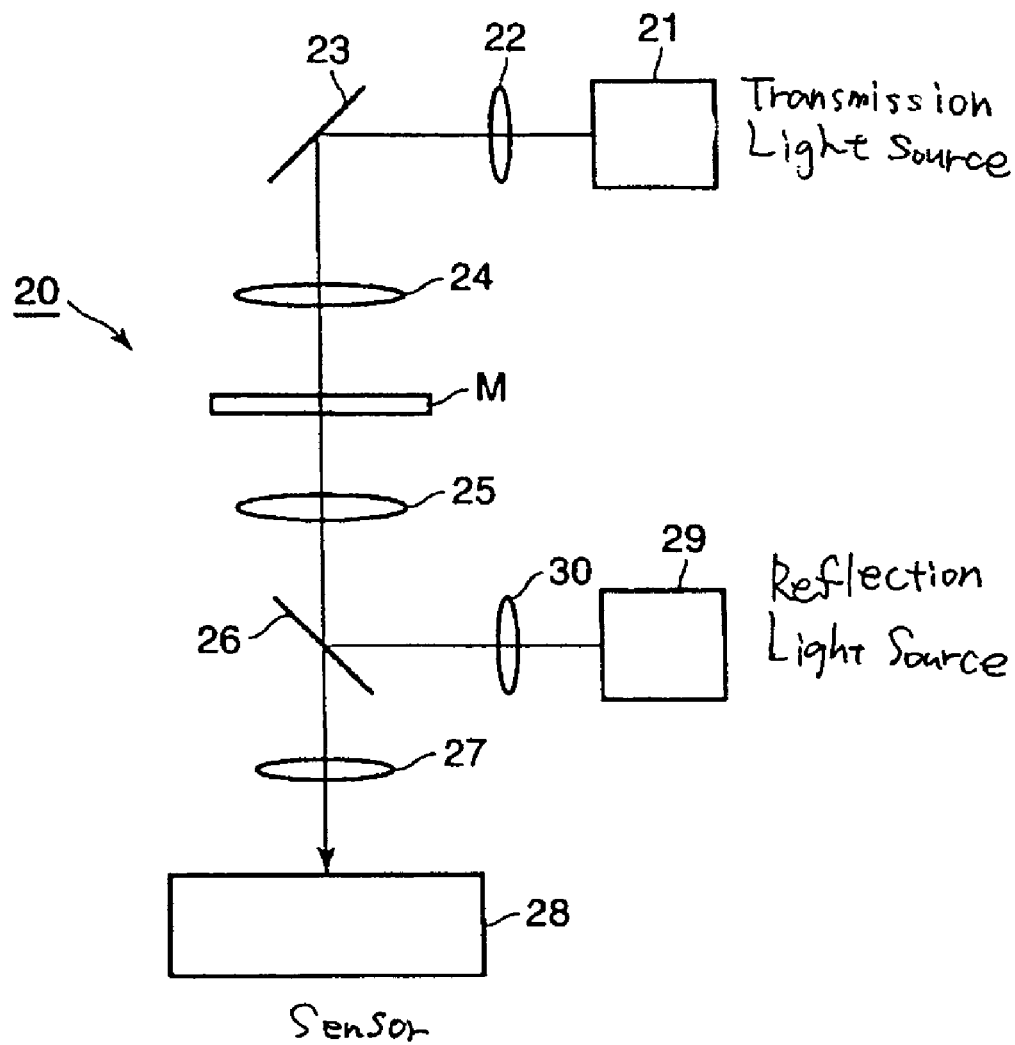
FIG. 11 shows a schematic diagram of a conventional inspecting apparatus 20 having two light sources.
Figure 12:
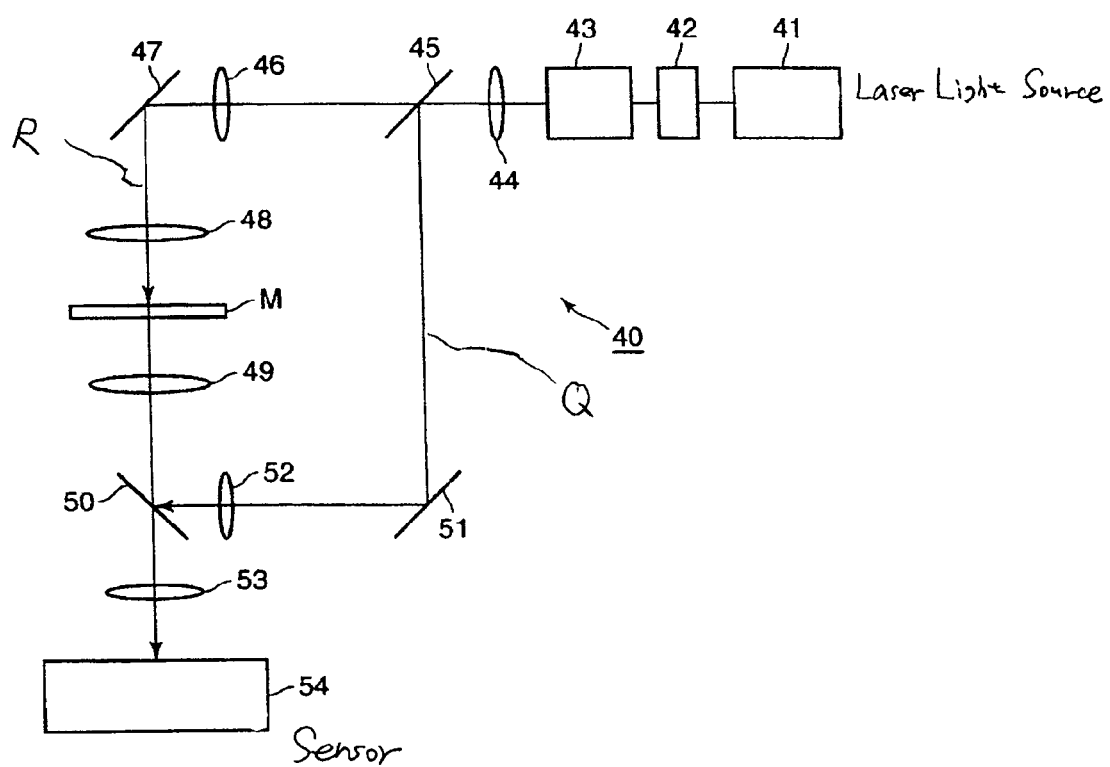
FIG. 12 shows a schematic diagram of a conventional inspecting apparatus 40 having a laser light sources.
Figure 13:
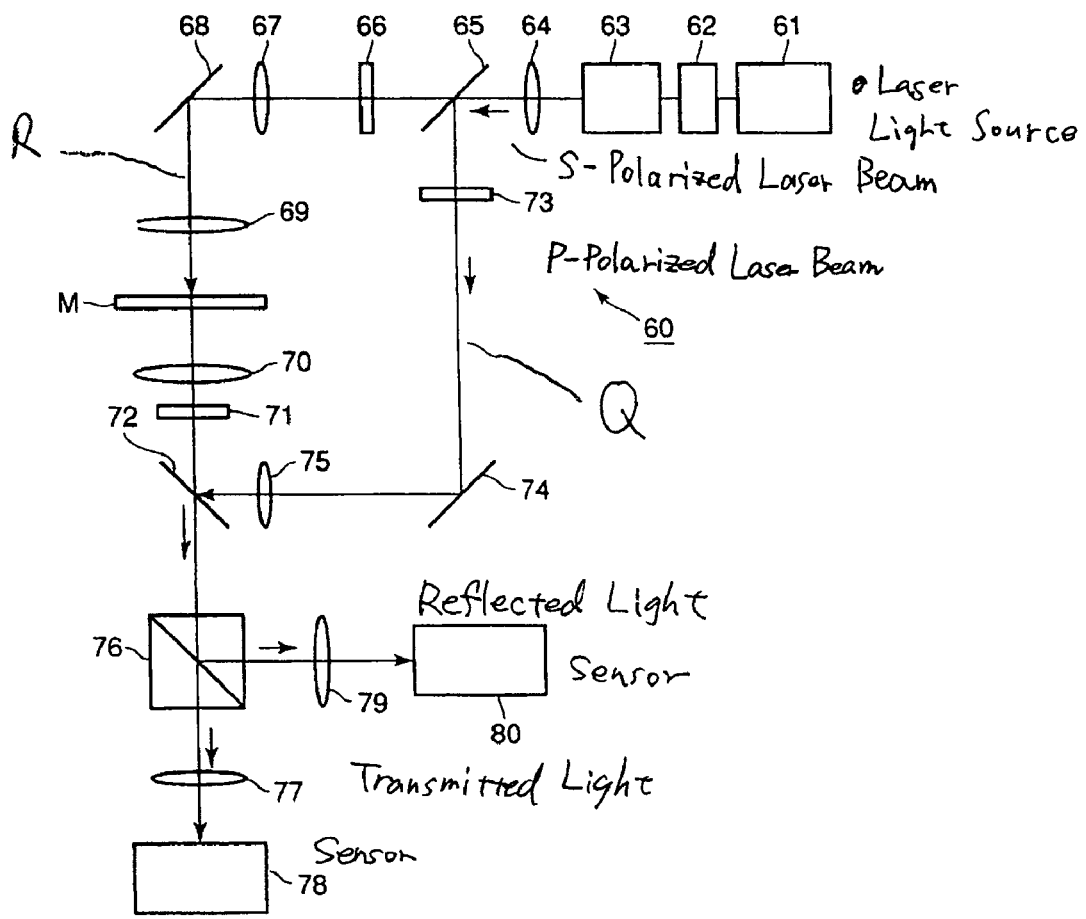
FIG. 13 shows a schematic diagram of a conventional inspecting apparatus 60 having laser light sources and two sensors.

FIG. 9 illustrates a schematic diagram of a mask inspection apparatus 200 consistent with a second embodiment of the present invention. The same reference characters are used to label the same or similar features of in both inspection apparatus 100 and inspection apparatus 200.

Mask inspection apparatus 200 is provided with a laser source 201 to expose an object, such as mask M instead of transmission and reflection light sources 111 and 121 shown in FIG. 1. Apparatus 200 also includes a beam expander 202 and a speckles reducing system 203. In addition, apparatus 200 includes an optical system 210 instead of second optical system 120. Further, optical system 210 includes half mirror 211, second aperture 212, a pair of collector lenses 213 and 214, and a mirror 215.

Half mirror 211 separates a laser beam emitted from light source 201 into laser beams for generating the transmitted and reflected images. Half mirror 132 directs laser beam H toward mask M, after laser beam H passes through collector 214.

Operation of mask inspection apparatus 200 will next be explained.

A laser beam passes through beam expander 202 and speckles reducing system 203 is separated into laser beam T and laser beam H by half mirror 211. Transmitted image of mask M is formed with laser beam T, and an exposed area of light beam H is reduced by second aperture 212. After passing through second aperture 212, light beam H exposes mask M to form a reflected image of mask M.

A transmitted image and a reflected image of mask M are sensed by sense device 140 via image optics 130, as in apparatus 100. A defect contained in mask M is detected by processor 150 and defect detecting circuit 160.

In mask inspection apparatus 200, a single light source 201 can be used to inspect mask M and has substantially the same advantages as apparatus 100 discussed above.

In addition to photolithography masks, other objects may be inspected. For example, any optical pattern or a flat display panel can be inspected with either apparatus 100 or 200.

As described above, apertures are used to block beams portions T and H to partially expose regions of mask M. The present invention, however, also contemplates exposing portions of a mask or other object with beams which have not been blocked by an aperture or other opaque device.

In addition, an area irradiated or exposed by light beam T and an area irradiated or exposed by light beam H, may have a small amount of overlap. In this invention, "spaced from" means separated or spaced from, as well as minimal overlap. Accordingly, images associated with beams T and H can be spaced from one another and minimally overlap one another as well. In addition the areas exposed by these beams may be separated or spaced from one another, and can also minimally overlap.

Numerous modifications of the present invention are possible in light of the above teachings. It is therefore to be understood that, within the scope of the appended claims, the present invention can be practiced in a manner other than as specifically described herein.

What is claimed is:

1. An apparatus configured to inspect an object, said apparatus comprising:
    a first optical system configured to expose a first portion of the object with a first light beam;
    a second optical system configured to expose a second portion of the object with a second light beam, the second portion of said object being substantially spaced from said first portion;
    a first sensor configured to sense a transmitted image of said first portion of said object, said transmitted image corresponding to a portion of said first light beam passing through said first portion of said object, and generate first image data in response to said transmitted image;
    a second sensor configured to sense a reflected image of said second portion of said object, said reflected image corresponding to a portion of said second light beam reflected off said second portion of said object, and generate second image data in response to said reflected image;
    a third optical system configured to focus said transmitted image on to said first sensor, and focus the reflected image on to the second sensor; and
    a defect detecting circuit configured to detect a defect of said object based upon said first and second image data,
    wherein the first optical system comprises a first aperture configured to block a portion of a first input light beam supplied to said first optical system, a remaining portion of said first input light beam corresponding to said first light beam, and said second optical system comprises a second aperture configured to block a portion of a second input light beam supplied to said second optical system, a remaining portion of said second input light beam corresponding to said second light beam.

2. An apparatus configured to inspect an object, said apparatus comprising:
    a first optical system configured to expose a first portion of the object with a first light beam;
    a second optical system configured to expose a second portion of the object with a second light beam, the second portion of said object being substantially spaced from said first portion;
    a first sensor configured to sense a transmitted image of said first portion of said object, said transmitted image corresponding to a portion of said first light beam passing through said first portion of said object, and generate first image data in response to said transmitted image;
    a second sensor configured to sense a reflected image of said second portion of said object, said reflected image corresponding to a portion of said second light beam reflected off said second portion of said object, and generate second image data in response to said reflected image;
    a third optical system configured to focus said transmitted image on to said first sensor, and focus the reflected image on to the second sensor; and
    a defect detecting circuit configured to detect a defect of said object based upon said first and second image data,
    wherein the first sensor and the second sensor are arranged adjacent one another.

3. An apparatus configured to inspect an object, said apparatus comprising:
    a first optical system configured to expose a first portion of the object with a first light beam;
    a second optical system configured to expose a second portion of the object with a second light beam, the second portion of said object being substantially spaced from said first portion;
    a first sensor configured to sense a transmitted image of said first portion of said object, said transmitted image corresponding to a portion of said first light beam passing through said first portion of said object, and generate first image data in response to said transmitted image;

a second sensor configured to sense a reflected image of said second portion of said object, said reflected image corresponding to a portion of said second light beam reflected off said second portion of said object, and generate second image data in response to said reflected image;

a third optical system configured to focus said transmitted image on to said first sensor, and focus the reflected image on to the second sensor; and a defect detecting circuit configured to detect a defect of said object based upon said first and second image data, wherein the first sensor and the second sensor are integrally manufactured on one wafer.

4. An apparatus configured to inspect an object, said apparatus comprising:

a first light source configured to emit a first input light beam to a first optical system, and a second light source configured to emit a second input light beam to a second optical system, the first optical system configured to expose a first portion of the object with the first light beam, the second optical system configured to expose a second portion of the object with the second light beam, and the second portion of said object being substantially spaced from said first portion;

a first sensor configured to sense a transmitted image of said first portion of said object, said transmitted image corresponding to a portion of said first light beam passing through said first portion of said object, and generate first image data in response to said transmitted image;

a second sensor configured to sense a reflected image of said second portion of said object, said reflected image corresponding to a portion of said second light beam reflected off said second portion of said object, and generate second image data in response to said reflected image;

a third optical system configured to focus said transmitted image on to said first sensor, and focus the reflected image on to the second sensor; and a defect detecting circuit configured to detect a defect of said object based upon said first and second image data, wherein the first optical system comprises a first aperture configured to block a portion of a first input light beam supplied to said first optical system, a remaining portion of said first input light beam corresponding to said first light beam, and said second optical system comprises a second aperture configured to block a portion of a second input light beam supplied to said second optical system, a remaining portion of said second input light beam corresponding to said second light beam.

5. A method for inspecting an object comprising the steps of:

generating a first light beam by blocking a portion of a first input light beam supplied to a first optical system;

outputting the first light beam from the first optical system;

generating a second light beam by blocking a portion of a second input light beam supplied to a second optical system;

outputting the second light beam from the second optical system;

exposing a first portion of said object with the first light beam;

exposing a second portion of said object with the second light beam, the second portion being spaced from the first portion;

sensing a transmitted image of a mask with a first sensor, said transmitted image corresponding to a portion of said first light beam passing through said object;

sensing a reflected image of the mask with a second sensor, said reflected image corresponding to a portion of said second light beam reflected off said object; and outputting signals representing data of the transmitted and reflected images so as to detect defects associated with said object based upon said transmitted and reflected images.

6. A method for inspecting an object, comprising:

exposing a first portion of said object with a first light beam;

exposing a second portion of said object with a second light beam, the second portion being spaced from the first portion;

sensing a transmitted image of a mask with a first sensor, said transmitted image corresponding to a portion of said first light beam passing through said object;

sensing a reflected image of the mask with a second sensor, said reflected image corresponding to a portion of said second light beam reflected off said object; and outputting signals representing data of the transmitted and reflected images so as to detect defects associated with said object based upon said transmitted and reflected images, wherein the first sensor and the second sensor are provided adjacent one another.

7. A method for inspecting an object, comprising:

exposing a first portion of said object with a first light beam;

exposing a second portion of said object with a second light beam, the second portion being spaced from the first portion;

sensing a transmitted image of a mask with a first sensor, said transmitted image corresponding to a portion of said first light beam passing through said object;

sensing a reflected image of the mask with a second sensor, said reflected image corresponding to a portion of said second light beam reflected off said object; and outputting signals representing data of the transmitted and reflected images so as to detect defects associated with said object based upon said transmitted and reflected images, wherein the first sensor and the second sensor are integrally manufactured on one wafer.

8. A method for inspecting an object, comprising:

generating a source beam;

dividing said source beam into first and second input beams;

blocking a portion said first input beam to output said first light beam;

blocking a portion of said second input beam to output said second light beam;

exposing a first portion of said object with the first light beam;

exposing a second portion of said object with the second light beam, the second portion being spaced from the first portion;

sensing a transmitted image of a mask with a first sensor, said transmitted image corresponding to a portion of said first light beam passing through said object;

sensing a reflected image of the mask with a second sensor, said reflected image corresponding to a portion of said second light beam reflected off said object; and outputting signals representing data of the transmitted and reflected images so as to detect defects associated with said object based upon said transmitted and reflected images.

* * * * *